(12) United States Patent
Jun et al.

(10) Patent No.: US 6,248,795 B1
(45) Date of Patent: Jun. 19, 2001

(54) PROCESS OF PREPARING A MIXTURE OF DIMETHYL ETHER AND METHANOL FROM CARBON DIOXIDE

(75) Inventors: Ki Won Jun; Kyu Wan Lee, both of Daejeon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 09/529,132
(22) PCT Filed: Mar. 6, 1998
(86) PCT No.: PCT/KR98/00042
§ 371 Date: Jun. 16, 2000
§ 102(e) Date: Jun. 16, 2000
(87) PCT Pub. No.: WO99/19287
PCT Pub. Date: Apr. 22, 1999

(30) Foreign Application Priority Data

Oct. 10, 1997 (KR) ........................................... 52169

(51) Int. Cl.$^7$ ..................................................... C07C 27/00
(52) U.S. Cl. .......................... 518/713; 518/700; 518/714; 518/728; 502/307; 502/343; 502/345; 502/342; 502/346
(58) Field of Search ..................................... 518/713, 714, 518/728, 700; 502/343, 345, 342, 346, 307

(56) References Cited

U.S. PATENT DOCUMENTS

| | | | |
|---|---|---|---|
| 4,366,260 | 12/1982 | Wainwright et al. | 518/713 |
| 5,254,596 | 10/1993 | Irick, Jr. et al. | 518/728 |
| 5,389,689 | 2/1995 | Fujimoto et al. | 518/700 |
| 5,393,793 | 2/1995 | Inue | 518/713 |

OTHER PUBLICATIONS

K. Jun et al., "Effective Conversion of $CO_2$ To Methanol and Dimethyl Ether Over Hybrid Catalysts", Chemical Abstracts, vol. 117, No. 10, Abstract No. 92606n, Kyoto International Conference Hall, Kyoto, Japan, (1997), (References,[1] J.–L. Dubois et al., Chem. Lett., 1115 (1992).
J.–L. Dubois et al., "Conversion of carbon dioxide to dimethyl ether and methanol over hybrid catalysts," Chem. Lett., (7) 1115–1118 (1992).
J.–L. Dubois et al., "Conversion of carbon dioxide to dimethyl ether and methanol over hybrid catalysts," Chemical Abstracts vol. 117, No. 10, Abstract No. 92606n (1992).
Ki–Won Jun et al., "Effective conversion of $CO_2$ to methanol and dimethyl ether over hybrid catalyst," Fourth International Conference on Carbon Dioxide Utilization (ICCDU IV), Sep. 7–11, 1997.
Ki–Won Jun et al., Effective conversion of $CO_2$ to methanol and dimethyl ether over hybrid catalyst, Studies in Surface Science and Catalysis, (114), 447–450 (1998).
Ki–Won Jun et al., Effective conversion of $CO_2$ to methanol and dimethyl ether over hybrid catalyst, Chemical Abstracts vol. 129, Abstract No. 42532 (1998).

*Primary Examiner*—Paul F. Shaver
(74) *Attorney, Agent, or Firm*—Finnegan, Henderson, Farabow, Garrett & Dunner, L.L.P.

(57) ABSTRACT

This invention relates to the process of preparing from carbon dioxide a mixture of dimethyl ether and methanol which are useful as clean fuel or raw materials in the chemical industry. More particularly, this invention relates to the process of preparing dimethyl ether and methanol in high yield without by-products such as hydrocarbons by means of chemical conversion of carbon dioxide, which is a major pollutant of the global environment, in the presence of a mixture of catalysts comprising Cu/ZnO-based catalyst and Y-type zeolite catalyst having a strong acidity with the $pK_a$ value of −6.0−−3.0.

7 Claims, No Drawings

PROCESS OF PREPARING A MIXTURE OF DIMETHYL ETHER AND METHANOL FROM CARBON DIOXIDE

BACKGROUND OF THE INVENTION

1. Field of the Invention

This invention relates to the process of preparing from carbon dioxide a mixture of dimethyl ether and methanol which are useful as clean purifying fuel or raw materials in the chemical industry. More particularly, this invention relates to the process of preparing dimethyl ether and methanol in high yield without by-products such as hydrocarbons by means of chemical conversion of carbon dioxide, which is a major pollutant of the global environment, in the presence of a mixture of catalysts comprising Cu/ZnO based catalyst and y-type zeolite catalyst having a strong acidity with the $pK_a$ value of −6.0−−3.0.

2. Description of the Prior Art

Carbon dioxide is a greenhouse gas which influences the global environment in a significant manner. Recently, it has been reported that the current global warming phenomenon induced by such greenhouse gas is attributable to various adverse effects in global environment including a unusual change of weather around the world (damages in agricultural plants due to unusual change of weather, changes of the precipitation level, ecological destruction, rise in sea water level, etc.). It is presumed that the global warming phenomenon may be lethal to the existence of the mankind at some point in the future.

The concentration of carbon dioxide in air has gradually increased to the level of 353 ppm as compared to 280 ppm in the pre-industrial revolution period. In an effort to adequately preserve the global environment, more active measures should be taken on a worldwide basis so as to prevent the increasing concentration of carbon dioxide in air. In this context, there has been a conspicuous trend to regulate the use of fossil fuels or the amount of carbon dioxide generation. In light of the current industrial system, one may expect the prolonged use of fossil fuels or other chemicals, giving rise to the generation of carbon dioxide. Under such circumstances, there is an urgent need for developing a process of converting carbon dioxide into useful fuels or compounds by recycling carbon dioxide generated by the combustion of fossil fuels. According to the actual statistics, since nations in the world are dependent on the fossil fuels (e.g., petroleum or coal) to the level of 73% of the total energy source, it can be safely said that the radical reduction of carbon dioxide source is nearly impossible.

Consequently, the development of clean fuels as a substitute for the fossil fuels is suggested in order to reduce the discharged amount of carbon dioxide. Alternatively, the methods of recovering and recycling the discharged carbon dioxide are put forth as a transient or supplemental measure. In parallel with this trend, much of the research have focused on the recovering and recycling carbon dioxide around the world.

As for the method of recovering and recycling carbon dioxide, carbon dioxide may be converted into a novel chemical material through chemical, biological, optical or electrochemical methods. With respect to above methods, the related studies have been numerously reported in the past. In order to recover a large amount of carbon dioxide discharged into air for the purposes of the consequent reaction, the pertinent reaction rate should be extremely rapid, and the final products should embrace a wide scope of market demand. Among these methods, the chemical conversion process of carbon dioxide has been reported to be most appropriate, and there is a market demand for converting carbon dioxide into widely applicable basic materials in the chemical industry or energy-based products instead of a small amount of chemical products.

As for the mass scale synthesis of the basic materials such as methanol, hydrocarbon, etc. from the chemically stable carbon dioxide, the reduction method using hydrogen in the presence of catalyst may be easily developed based on the current technology. Thus, the research on the topic of actually synthesizing methanol from carbon dioxide and hydrogen have been actively carried out, and there have been a great number of studies reporting the use of the catalyst system containing Cu/ZnO as basic constituent.

In the case where methanol is synthesized by chemical conversion of carbon dioxide, the copper-based catalysts are employed, and two reactions as shown in the following schemes 1 and 2 occur on a parallel basis.

Scheme 1

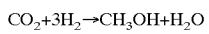
$$CO_2 + 3H_2 \rightarrow CH_3OH + H_2O$$

Scheme 2

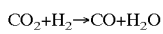
$$CO_2 + H_2 \rightarrow CO + H_2O$$

As noted in the above schemes 1 and 2, these simultaneous reactions are subject to thermodynamic limit, and the conversion rate of carbon dioxide into methanol and the selectivity among the reaction products of the generated methanol have constant equilibrium values as function of temperature and pressure. When methanol is synthesized from carbon dioxide, the low conversion rate of carbon dioxide into methanol requires the recycling of carbon dioxide in a large amount, and this is not preferable in the manufacturing process.

To resolve this matter, much of the endeavors have been made so as to overcome the low conversion rate of carbon dioxide owing to such thermodynamic limit, i.e., a simultaneous execution of the reaction designed to synthesize methanol from carbon dioxide and the reaction of converting methanol, so formed, into the second dimethyl ether, as shown in the following scheme 3. As such, by reducing the amount of methanol within a reactor, the thermodynamic limit is alleviated, which in turn leads to the improvement of the conversion rate of carbon dioxide and simultaneous generation of methanol and dimethyl ether.

Scheme 3

$$2CH_3OH \rightarrow CH_3OCH_3 + H_2O$$

Dimethyl ether, an intermediate generated in the MTG (methanol to gasoline) process of preparing various hydrocarbons from methanol, has a high potential use as a basic material in the chemical industry in addition to being a highly effective clean fuel. Presently, there is a possibility that dimethyl ether may be substituted as a clean fuel for the internal combustion engine. As such, the reaction for generating dimethyl ether directly from carbon dioxide may provide two advantages as follows: 1) the process conversion rate of carbon dioxide may be improved, and 2) the utility of dimethyl ether, so formed, is not inferior to that of methanol. Furthermore, since there is a significant difference in boiling point between dimethyl ether and methanol, the separation is easily obtained for manufacturing thereof.

J. L. Dubois et al. discloses a process for preparing dimethyl ether and methanol from carbon dioxide and hydrogen using a catalyst consisting of $Cu/ZnO/Al_2O_3$ catalyst and Y-type zeolite [Chem. Lett., 1115 (1992)]. According to this method, HY-type zeolite for commercial use was employed without modification. However, according to the studies by the inventors herein, HY-type zeolite with extremely strong acidity ($pKa \geq -8.2$) may result in generating hydrocarbon by-products such as methane, ethane, propane, etc. The generated hydrocarbons as by-product belong to the alkane group with low molecular weight and have recognized disadvantages in that a) their utility is less significant as reaction products, b) it is not easy to separate some of the hydrocarbons from carbon dioxide during the separation process of the reactions products after said reactions. Therefore, even though a small amount of hydrocarbons is generated, the recycling process of unreacted carbon dioxide causes the continual accumulation of by-products (e.g., hydrocarbon, etc.) within the reaction gas, whereby affecting the process steps in a negative manner.

SUMMARY OF THE INVENTION

The inventors of the invention herein have endeavored to overcome some of the shortcomings associated with the conventional method of preparing methanol and dimethyl ether from hydrogenation of carbon dioxide in the presence of a catalyst mixture consisting of $Cu/ZnO/Al_2O_3$ catalyst and HY-type zeolite, as suggested by J. L. Dubois et al. As a result, the inventors herein have devised said invention based on the following facts: First, Y-type zeolite is pretreated to have a strong acidity of approximately $-6.0$–$-3.0$ as a $pK_a$ value by means of substitution with an appropriate metal cation. Then, said Y-type zeolite is employed as catalyst in the hydrogenation of carbon dioxide together with Cu/ZnO-based catalyst. Consequently, the final products exhibit relatively high catalytic activities without formation of hydrocarbon by-products, and this may contribute to the improvement in the conversion rate as a mixture containing both methanol and dimethyl ether.

Therefore, the objective of this invention is to provide a process for preparing a mixture of dimethyl ether and methanol from hydrogenation of carbon dioxide.

DETAILED DESCRIPTION OF THE INVENTION

This invention relates to a process for preparing dimethyl ether and methanol via hydrogenation of carbon dioxide in the presence of a catalyst comprising Cu/ZnO-based catalyst and Y-type zeolite catalyst having a strong acidity with $-6.0$–$-3.0$ as a $pK_a$ value.

This invention is explained in more detail as set forth hereunder.

This invention relates to the process of preparing a mixture of dimethyl ether and methanol via unique composition of a catalyst mixture, wherein said scheme 3 is added to the parallel reaction process as shown in the schemes 1 and 2. Consequently, said process results in better yield as compared to the sole production of methanol without by-products such as hydrocarbons.

In line with the catalyst mixture system selected from this invention, Cu/ZnO-based catalyst is mainly involved in the reaction of converting carbon dioxide into methanol. Any catalysts containing Cu/ZnO as basic ingredient may be freely used, but it is preferable to use $Cu/ZnO/Al_2O_3$ and $Cu/ZnO/Cr_2O_3$.

Further, the Y-type zeolite catalyst having a strong acidity of $-6.0$–$-3.0$ as $pK_a$ value is mainly involved in the reaction of converting methanol into dimethyl ether. In particular, the reaction of converting methanol into dimethyl ether is performed by acid catalyst. Due to the fact that the formation of dimethyl ether corresponds to the intermediate-formation step of hydrocarbon, the activity and selectivity of catalyst may differ depending upon the $pK_a$ value of acid catalyst. For example, in case of a catalyst having a strong acidity of less than $-6.0$ as a $pK_a$ value, an additional reaction is carried out to form hydrocarbons after the formation step of dimethyl ether from methanol, the result of which is the production of hydrocarbons as by-product. In case of a catalyst having a weak acidity of more than $-3.0$ as a $pK_a$ value, the catalytic activity is low so that the reaction of converting methanol into dimethyl ether may be insufficient.

The commonly used Y-type zeolite includes NaY-type zeolite and HY-type zeolite which contain $Na^+$ and $H^+$, respectively, as cations. However, according to the studies by the inventors herein, the NaY-type zeolite retaining the weak-acid sites ($pK_a > 4.0$) has proven to be inefficient while HY-type zeolite which has been ion-exchanged with $H^+$ produces hydrocarbons as by-product due to its extremely strong-acid sites ($pK_a \leq -8.2$).

Under the invention herein, Y-type zeolite is ion-exchanged with appropriate metal ions in such a manner that the mixture status of cation is achieved with a strong acidity of $-6.0$–$-3.0$ as a $pK_a$ value. For example, the HY-type zeolite having a strong acidity ($pKa \geq 8.2$) may be appropriately ion-exchanged with a sodium ion for preparing NaHY-type zeolite. Further, a copper ion or zinc ion may appropriately ion-exchanged for preparing CuHY-type or ZnHY-type zeolite. NaY-type zeolite having only a weak acidity ($pKa > +4.0$) may be ion-exchanged with a copper ion or zinc ion for preparing CuNaY-type or ZnNaY-type zeolite.

With the aforementioned method, the existing problems can be completely solved. No change has been observed on the activity of catalyst related to formation of dimethyl ether, and as a result, a mixture of dimethyl ether and methanol is formed without any formation of hydrocarbons as by-product.

Based on the process for the preparation, this invention is explained in more detail as set forth hereunder.

Cu/ZnO-based catalyst used in this invention is a mixed oxide obtained in such a manner that active metal salts, such as copper ion and zinc ion, are mixed with sodium carbonate in an aqueous solution, and the product, so precipitated, is calcined. Such catalyst may be prepared by a commonly available method. For example, $Cu/ZnO/Al_2O_3$ catalyst may be obtained using copper nitrate, zinc nitrate and aluminum nitrate while $Cu/ZnO/Cr_2O_3$ catalyst may be obtained using copper nitrate, zinc nitrate, and chromic nitrate.

Further, according to this invention, an ion-exchange method using metal ion is selected as the method of adjusting the acidity (pKa) of Y-type zeolite, and the above method is based on the commonly available ion-exchange method.

CuNaY-type zeolite is prepared in such a manner that NaY-type zeolite is ion-exchanged in an aqueous salt solution containing copper such as cupric chloride or cupric nitrate, after which said zeolite is dried and calcined. ZnNaY-type zeolite is prepared in such a manner that NaY-type zeolite is ion-exchanged in an aqueous salt solution containing zinc such as zinc chloride or zinc nitrate, after which is dried and calcined. NaHY-type zeolite is prepared in such a manner that $NH_4Y$-type zeolite is ion-exchanged in an aqueous salt solution containing sodium such as sodium chloride or sodium nitrate, after which is dried and calcined. CuHY-type zeolite is prepared in such a manner that $NH_4Y$-type zeolite is ion-exchanged in an aqueous salt solution containing copper such as cupric chloride or cupric nitrate, after which is dried and calcined. Further, ZnHY-type zeolite is prepared in such a manner that $NH_4Y$-type zeolite is ion-exchanged in an aqueous salt solution containing zinc such as zinc chloride or zinc nitrate, after which is dried and calcined.

Hence, the $pK_a$ value may differ depending on the ion-exchange amount of Y-type zeolite. In order to prepare Y-type zeolite catalyst having a strong acidity of −6.0–−3.0 as a $pK_a$ value according to this invention, it is preferable to have 30–90% of sodium ion to be ion-exchanged for NaHY-type zeolite. As for CuNaY-type, ZnNaY-type, CuHY-type or ZnHY-type zeolite, it is preferable to have 50–90% of copper ion or zinc ion to be ion-exchanged.

As aforementioned, after the catalyst mixture is packed into a reactor, and prior to main hydrogenation, the pre-treatment for reduction using hydrogen gas is performed so as to activate the catalyst. The pre-treatment process is carried out in a reactor by passing hydrogen or diluted hydrogen gas at a flow rate of 20–100 ml/g-catalyst/min at 200–350° C. When such pre-treatment process is completed, cupric oxide (CuO) which consists of of Cu/ZnO-based catalyst, is reduced to metal copper (Cu). Further, when the catalyst mixture is packed into a reactor, it is preferred that Cu/ZnO-based catalyst and Y-type zeolite with adjusted strong-acidity be maintained in the weight ratio of 1:0.5–1:2, so as to effectively carry out the whole reaction by maintaining the balance between the reactions of methanol and dimethyl ether formations.

A gas mixture consisting of carbon dioxide and hydrogen is passed through a reactor in the presence of the catalyst, followed by the above pre-treatment process. It is preferred that the mixing ratio ($H_2/CO_2$) of both carbon dioxide and hydrogen in raw gas be maintained in the volumetric ratio of 1.0–5.0 since the mixing ratio ($H_2/CO_2$) for the stoichiometric amount in the reaction for the formation of methanol and dimethyl ether from the hydrogenation of carbon dioxide is determined to be the volumetric ratio of 3. Thus, if the above range is significantly exceeded, the higher conversion rate may be not expected.

As aforementioned, both catalyst mixture and gas mixture are packed into a reactor. Then, the reaction is performed under an appropriate temperature, pressure and velocity in space. The reaction temperature is generally maintained in the range of 150–350° C. If the temperature is less than 150° C., the insufficient reaction rate may lead to a lower conversion rate. On the other hand, if it exceeds 350° C., this may thermodynamically prevent the formation of dimethyl ether, the result of which is the lower conversion rate. The reaction pressure is generally maintained in the rage of 10–100 atm. If the pressure is less than 10 atm, this may thermodynamically prevent formation of dimethyl ether with the result of the extremely low reaction rate. On the other hand, if it exceeds 100 atm, this is not suitable due to the operation problem of the reaction. Further, as for velocity in space, it is preferred to perform the hydrogenation of carbon dioxide in the range of 500–50,000 $h^{-1}$. If the space velocity of the gas mixture is less than 500 $h^{-1}$, the reaction productivity is extremely low. If it exceeds 50,000 $h^{-1}$, a shortened contact time with the catalyst results in the lower conversion rate. The reactor of this invention may include a gaseous phase fixed-bed reactor, fluidized-bed reactor, or liquid phase slurry-type reactor. The same effect can be obtained even if other reactors are used.

As mentioned above, according to this invention, a catalyst mixture containing Cu/ZnO-based catalyst and Y-type zeolite having adjusted strong-acidity is activated via pre-treatment for reduction using hydrogen gas, and under appropriate reaction conditions, the reaction between carbon dioxide and hydrogen is carried out. Thus, this invention has some advantages in that both dimethyl ether and methanol may be simultaneously prepared in high yield without any formation of hydrocarbons as by-product.

This invention is explained in more detail by the following examples but is not limited by the examples herein.

EXAMPLE 1

A mixture of $Cu(NO_3)_2.3H_2O$ (13.2 g), $Zn(NO_3)_2.6H_2O$ (11.4 g) and $Cr(NO_3)_3.9H_2O$ (1.83 g) was dissolved in distilled water to produce 100 ml of metal nitrate aqueous solution. Sodium carbonate (10.6 g) was dissolved in distilled water to produce a solution of 100 ml. The metal nitrate solution was mixed with sodium carbonate to form a precipitate. The precipitate was filtered and washed with distilled water. The precipitate, so formed, was dried at 120° C. and calcined at 350° C. for 5 hours in air to yield $Cu/ZnO/Cr_2O_3$ catalyst.

$NH_4Y$ zeolite was added to 100 ml aqueous solution of 0.1N sodium chloride and stirred at 80° C. for 24 hours. The resulting suspension was filtered, washed with distilled water and dried at 120° C. for 12 hours. The resulting solid was calcined at 500° C. for 12 hours to yield NaHY-type zeolite (Na ion-exchange rate=44%, $pK_a \geq -5.6$).

Both $Cu/ZnO/Cr_2O_3$ catalyst and NaHY-type zeolite were molded in the size of 60–80 mesh using a pelletizer. Then, 0.5 g of each material was collected, mixed homogeneously and packed into a fixed-bed reactor. Under this state, a gas mixture consisting of 10% hydrogen and nitrogen was passed at a rate of 50 ml/min, and a catalyst mixture was pretreated for reduction at 250° C. A gas mixture consisting of carbon dioxide and hydrogen ($H_2:CO_2=3:1$ in volumetric ratio) was passed into the catalyst mixture bed at 270° C. under 30 atm and at a space velocity of 1,200 $h^{-1}$. The reaction results are shown in the following table 1.

EXAMPLE 2

Under the same procedure as described in Example 1, a catalyst mixture was prepared, provided, however, that when NaHY-type zeolite was prepared, 0.5N sodium chloride solution was employed (Na ion-exchange rate=78%, $pK_a \geq -5.6$). Further, under the same procedure as described in Example 1, the catalyst mixture was pretreated for reduction, and the reaction was subsequently carried out. The reaction results are shown in the following table 1.

EXAMPLE 3

Under the same procedure as described in Example 1, $Cu/ZnO/Cr_2O_3$ catalyst was prepared.

NaY zeolite was added to 100 ml aqueous solution of 1N sodium chloride and stirred at 80° C. for 24 hours. The resulting suspension was filtered and washed with distilled water. The resulting solid was dried at 120° C. for 12 hours, again added to 100 ml aqueous solution of 1N sodium chloride and ion-exchanged under the same procedure as above. Then, through the process of filtration, washing and drying, the mixture was calcined at 500° C. for 12 hours to yield NaHY-type zeolite (Na ion-exchange rate=88%, $pK_a \geq -3.0$).

Further, under the same procedure as described in Example 1, the catalyst mixture was pretreated for reduction, and the reaction subsequently was carried out. The reaction results are shown in the following table 1.

EXAMPLE 4

Under the same procedure as described in Example 1, Cu/ZnO/Cr$_2$O$_3$ catalyst was prepared.

NaY zeolite was added to 100 ml aqueous solution of 0.5N cupric nitrate and stirred at 80° C. for 24 hours. The resulting suspension was filtered, washed with distilled water. The resulting solid was dried at 120° C. for 12 hours, again added to 100 ml aqueous solution of 0.5N cupric nitrate, and ion-exchanged under the same procedure as above. Then, through the process of filtration, washing and drying processes, the solid was calcined at 500° C. for 12 hours to yield CuNaY-type zeolite (Cu ion-exchange rate=72%, pK$_a$≧−5.6).

Further, under the same procedure as described in Example 1, the catalyst mixture was pretreated for reduction, and the reaction was subsequently carried out. The reaction results are shown in the following table 1.

EXAMPLE 5

Under the same procedure as described in the Example 1, Cu/ZnO/Cr$_2$O$_3$ catalyst was prepared.

NaY zeolite was added to 100 ml aqueous solution of 0.5N zinc nitrate and stirred at 80° C. for 24 hours. The resulting suspension was filtered, washed with distilled water and dried at 120° C. for 12 hours. The resulting solid was dried at 120° C. for 12 hours, again added to 100 ml aqueous solution of 0.5N zinc nitrate, and ion-exchanged under the same procedure as above. Then, through the process of filtration, washing and drying processes, the solid was calcined at 500° C. for 12 hours to yield ZnNaY-type zeolite (Zn ion-exchange rate=70%, pK$_a$≧−5.6).

Further, under the same procedure as described in Example 1, the catalyst mixture was pretreated for reduction, and the reaction was subsequently carried out. The reaction results are shown in the following table 1.

EXAMPLE 6

Under the same procedure as described in Example 1, CuO/ZnO/Cr$_2$O$_3$ catalyst was prepared.

NH$_4$Y zeolite was added to 100 ml aqueous solution of 0.5N cupric nitrate and stirred at 80° C. for 24 hours. The resulting suspension was filtered, washed with distilled water and dried at 120° C. for 12 hours. The resulting solid was again added to 100 ml aqueous solution of 0.5N cupric nitrate and was to ion-exchanged in the same procedure as above. Then, through the processes of filtration, washing and drying processes, the solid was calcined at 500° C. for 12 hours to yield CuHY-type zeolite (Cu ion-exchange rate=80%, pKa≧−5.6).

Further, in the same procedure as described in Example 1, the catalyst mixture was pretreated for reduction, and the reaction was subsequently carried out. The reaction results are shown in the following table 1.

EXAMPLE 7

Under the same procedure as described in Example 1, Cu/ZnO/Cr$_2$O$_3$ catalyst was prepared.

NH$_4$Y zeolite was added to 100 ml aqueous solution of 0.5N zinc nitrate and stirred at 80° C. for 24 hours. The resulting suspension was filtered, washed with distilled water. The resulting solid was dried at 120° C. for 12 hours, again added to 100 ml aqueous solution of 0.5N zinc nitrate, and ion-exchanged under the same procedure as above. Then, through the process of filtration, washing and drying processes, the solid was calcined at 500° C. for 12 hours to yield ZnHY-type zeolite (Zn ion-exchange rate=73%, pK$_a$≧−5.6).

Further, in the same procedure as described in Example 1, the catalyst mixture was pretreated for reduction, and the reaction subsequently was carried out. The reaction results are shown in the following table 1.

EXAMPLE 8

Under the same procedure as described in Example 4, a catalyst was prepared for said reaction. When both carbon dioxide and hydrogen were passed through catalyst bed for reaction, the reaction temperature was adjusted to 250° C. The reaction results are shown in the following table 1.

EXAMPLE 9

Under the same procedure as described in the Example 4, a catalyst was prepared for said reaction. When both carbon dioxide and hydrogen were passed through catalyst bed for reaction, the space velocity was 1,490 h$^{-1}$. The reaction results are shown in the following table 1.

EXAMPLE 10

Under the same procedure as described in Example 4, a catalyst was prepared for said reaction. When both carbon dioxide and hydrogen were passed through catalyst bed for reaction, the reaction temperature and space velocity were 250° C. and 1,490 h$^{-1}$, respectively. The reaction results are shown in the following table 1.

EXAMPLE 11

A mixture of Cu(NO$_3$)$_2$.3H$_2$O (12.8 g), Zn(NO$_3$)$_2$.6H$_2$O (11.1 g) and Al(NO$_3$)$_3$.9H$_2$O (2.47 g) was dissolved in distilled water to produce 100 ml metal nitrate solution. Sodium carbonate (10.6 g) was dissolved in distilled water to produce a solution of 100 ml. The metal nitrate solution was mixed with sodium carbonate to form a precipitate. The precipitate was filtered and washed with distilled water The precipitate, so formed, was dried at 120° C. and calcined at 350° C. for 5 hours in air to yield Cu/ZnO/Al$_2$O$_3$ catalyst.

NaY zeolite was added to 100 ml aqueous solution of 0.5N cupric nitrate and stirred at 80° C. for 24 hours. The resulting suspension was filtered, washed with distilled water. The solid was dried at 120° C. for 12 hours, again added to 100 ml aqueous solution of 0.5N cupric nitrate, and ion-exchanged under the same procedure as above. Then, through the process of filtration, washing and drying processes, the mixture was calcined at 500° C. for 12 hours to yield CuNaY-type (Cu ion-exchange rate=72%, pK$_a$≧−5.6).

Both Cu/ZnO/Al$_2$O$_3$ catalyst and CuNaY-type zeolite, so prepared, were molded in the size of 60–80 mesh using a pelletizer. Then, 0.5 g of each material was collected, mixed homogeneously and packed into a fixed-bed reactor. Under this state, a gas mixture consisting of 10% hydrogen and nitrogen was passed at a rate of 50 ml/min, and a catalyst was pretreated for reduction at 250° C. A gas mixture consisting of carbon dioxide and hydrogen (H$_2$:CO$_2$3:1 in volumetric ratio) was passed into the catalyst bed at 270° C. under 30 atm and at the space velocity of 2,400 h$^{-1}$. The reaction results are shown in the following table 1.

Comparative Example 1

Under the same procedure as described in Example 1, the reaction was carried out using NaY zeolite without ion-exchange.

Comparative Example 2

Under the same procedure as described in Example 1, the reaction was carried out using HY zeolite without ion-exchange.

Comparative Example 3

Under the same procedure as described in Example 11, the reaction was carried out using NaY zeolite without ion-exchange.

Comparative Example 4

Under the same procedure as described in Example 11, the reaction was carried out using HY zeolite without ion-exchange.

TABLE 1

| Classification | Conversion rate* (mol%) | | | |
| --- | --- | --- | --- | --- |
| | Carbon monoxide | Methanol | Dimethyl ether | Hydrocarbon |
| Example 1 | 9.96 | 3.51 | 11.80 | 0 |
| Example 2 | 9.81 | 3.67 | 11.69 | 0 |
| Example 3 | 10.32 | 3.90 | 10.74 | 0 |
| Example 4 | 10.14 | 2.72 | 12.76 | 0 |
| Example 5 | 10.03 | 2.82 | 11.36 | 0 |
| Example 6 | 10.76 | 2.95 | 11.65 | 0 |
| Example 7 | 10.95 | 3.09 | 11.07 | 0 |
| Example 8 | 7.75 | 3.07 | 12.11 | 0 |
| Example 9 | 9.53 | 2.09 | 10.58 | 0 |
| Example 10 | 7.44 | 2.65 | 10.53 | 0 |
| Example 11 | 9.00 | 3.01 | 10.70 | 0 |
| Comparative Example 1 | 13.64 | 6.51 | 0.97 | 0 |
| Comparative Example 2 | 10.83 | 2.86 | 10.03 | 1.53 |
| Comparative Example 3 | 11.53 | 5.81 | 0.54 | 0 |
| Comparative Example 4 | 9.21 | 2.75 | 9.01 | 1.01 |

*The conversion rate represents the mol% of inserted carbon dioxide converted into the corresponding products; and unconverted carbon dioxide is recycled.

As noted in the above table 1, the process used in the invention herein shows that the yield of dimethyl ether was high without any formation of hydrocarbons as by-product. In contrast, when NaY-type zeolite (Comparative Example 1 and 3) having only weak acidity ($pK_a > +4.0$) is employed, no hydrocarbons were observed, but the lower conversion rate to dimethyl ether resulted in the low yield for the total formation of dimethyl ether and methanol. Further, when HY-type zeolite (Comparative Example 2 and 4) having strong acidity of up to $-8.2$ as a $pK_a$ value was employed, the conversion rate to dimethyl ether was high, but hydrocarbons as by-products were observed.

Hence, hydrocarbons, so generated as by-product, belong to the alkane group with low molecular weight and have recognized disadvantages in that a) their utility is less significant as reaction products, b) it is not easy to separate some of the hydrocarbons from carbon dioxide during the separation of the reaction products after said reaction. Consequently, during the recycling process of unreacted materials, said hydrocarbons are accumulated and mixed with the gas reactants with the result of affecting the manufacturing process in a negative manner by causing a change in the chemical composition of gas reactants and inefficiency in said manufacturing process.

As mentioned above, the invention herein employs a mixture of catalysts comprising Cu/ZnO-based catalyst and Y-type zeolite catalyst having a strong acidity with said $pK_a$. As a result, the yields of dimethyl ether and methanol are enhanced via higher catalytic activity without formation of hydrocarbons as by-products.

What is claimed is:

1. A process for preparing a mixture of dimethyl ether and methanol by hydrogenation of carbon dioxide in the presence of a mixture of catalysts comprising Cu/ZnO-based catalyst and Y-type zeolite catalyst having a strong acidity with $-6.0$ — $-3.0$ as a $pK_a$ value.

2. A process for preparing a mixture of dimethyl ether and methanol from carbon dioxide according to claim 1, wherein said Cu/ZnO-based catalyst is $Cu/ZnO/Cr_2O_3$ or $Cu/ZnO/Al_2O_3$.

3. A process for preparing a mixture of dimethyl ether and methanol from carbon dioxide according to claim 1, wherein said Y-type zeolite catalyst is a NaHY-type zeolite in which 30–90% of $H^+$ cation in HY-type zeolite has undergone an ion exchange by means of sodium ions.

4. A process for preparing a mixture of dimethyl ether and methanol from carbon dioxide according to claim 1, wherein said Y-type zeolite catalyst is a CuNaY-type zeolite in which 50–90% of $Na^+$ cation in NaY-type zeolite has undergone an ion-exchanged by means of copper ions.

5. A process for preparing a mixture of dimethyl ether and methanol from carbon dioxide according to claim 1, wherein said Y-type zeolite catalyst is a ZnNaY-type zeolite in which 50–90% of $Na^+$ cation in NaY-type zeolite has undergone an ion exchange by means of zinc ions.

6. A process for preparing a mixture of dimethyl ether and methanol from carbon dioxide according to claim 1, wherein said Y-type zeolite catalyst is CuHY-type zeolite in which 50–90% of $H^+$ cation in HY-type zeolite has undergone an ion exchange by means of copper ions.

7. A process for preparing a mixture of dimethyl ether and methanol from carbon dioxide according to claim 1, wherein said Y-type zeolite catalyst is ZnHY-type zeolite in which 50–90% of $H^+$ cation in HY-type zeolite has undergone an ion exchange by means of zinc ions.

\* \* \* \* \*

UNITED STATES PATENT AND TRADEMARK OFFICE
CERTIFICATE OF CORRECTION

PATENT NO. : 6,248,795 B1  
DATED : June 19, 2001  
INVENTOR(S) : Ki Won Jun et al.

Page 1 of 1

It is certified that error appears in the above-identified patent and that said Letters Patent is hereby corrected as shown below:

Title page,
Item [57], line 11, of ABSTRACT, "-6.0—3.0" should read -- -6.0~3.0 --.

Column 10, claim 1,
Line 23, "-6.0—3.0" should read -- 6.0~-3.0 --.

Column 10, claim 3,
Line 32, "3.0-90%" should read -- 30~90% --.

Column 10, claim 4,
Line 36, "50-90%" should read -- 50~90% --.

Column 10, claim 5,
Line 41, "50-90%" should read -- 50~90% --.

Column 10, claim 6,
Line 46, "50-90%" should read -- 50~90% --.

Column 10, claim 7,
Line 51 "50-90%" should read -- 50~90% --.

Signed and Sealed this

Twenty-ninth Day of January, 2002

*Attest:*

JAMES E. ROGAN
*Attesting Officer*     *Director of the United States Patent and Trademark Office*